United States Patent
Grieshaber et al.

[11] Patent Number: 6,149,274
[45] Date of Patent: Nov. 21, 2000

[54] METHOD OF AND APPARATUS FOR FOCUSING A LIGHT FLUX

[75] Inventors: Hans R. Grieshaber; Urs Vogel, both of Schaffhausen, Switzerland

[73] Assignee: Grieshaber & Co. AG Schaffhausen, Schaffhausen, Switzerland

[21] Appl. No.: 09/410,580

[22] Filed: Oct. 1, 1999

[30] Foreign Application Priority Data

Nov. 7, 1998 [CH] Switzerland ............................ 2235/98
Jan. 22, 1999 [CH] Switzerland ............................ 0120/99

[51] Int. Cl.$^7$ ...................................................... A61B 3/10
[52] U.S. Cl. .......................................................... 351/221
[58] Field of Search ........................... 351/221; 128/898; 606/4, 15, 16; 362/119, 572, 293; 385/19

[56] References Cited

U.S. PATENT DOCUMENTS

5,003,434  3/1991  Gonser ...................................... 362/572
5,203,353  4/1993  Easlet ....................................... 128/898

*Primary Examiner*—George Manuel
*Attorney, Agent, or Firm*—Henry M. Feiereisen

[57] ABSTRACT

An apparatus for focusing a light flux, includes a light source, and a light-conducting system which guides light radiating from the light source along a first light-conducting passageway oriented in a direction of the path of light, and along a second light-conducting passageway extending at an angle to the first light-conducting passageway. The light conducting system includes a first optical lens which is positioned at an entry side into the first light-conducting passageway, a deflector which is positioned at an exit side of the first light-conducting passageway for deflecting visible light into the second light-conducting passageway, and an optical assembly which is disposed in the second light-conducting passageway. The optical assembly is formed by an dimming disk, adjustable with respect to the second light-conducting passageway, for selective control of light intensity of the visible radiation, and a second optical lens for focusing the deflected radiation.

28 Claims, 6 Drawing Sheets

METHOD OF AND APPARATUS FOR FOCUSING A LIGHT FLUX

CROSS-REFERENCES TO RELATED APPLICATIONS

This application claims the priorities of Swiss Patent Applications, Serial No. CH 1998 2235/98, filed Nov. 7, 1998, and CH 1999 0120/99, filed Jan. 22, 1999, the subject matter of which are incorporated herein by reference.

BACKGROUND OF THE INVENTION

The present invention relates to a method of and apparatus for focusing a light flux radiating from a light source.

During examinations and/or surgical procedures on the eye, in particular during surgery of the vitreous body, the use of an illumination probe, normally in the form of a light guide of glass fibers or plastic fibers is generally known. The illumination probe is typically connected to a unit comprised of a light source in the form of a halogen lamp, and optical elements. Conventional units suffer the shortcomings that after a relatively brief period, the light source fails to maintain a sufficient illumination of the cavity of the vitreous body or becomes defective. Further drawbacks of conventional units include undesired side effects associated with the operation, for example, the relative intense heat generation of the light source.

SUMMARY OF THE INVENTION

It is thus an object of the present invention to provide an improved method and apparatus for focusing a light flux, obviating the afore-stated drawbacks.

In particular, it is an object of the present invention to provide an improved method and apparatus for focusing a light flux, without encountering excessive heat generation while accomplishing a substantially uniform diameter of the cone of light transmitted to an illumination probe.

These objects, and others which will become apparent hereinafter, are attained in accordance with the present invention by a method which comprises the steps of: directing a light flux by a first optical lens through a first light-conducting passageway onto a structure by which heat, at least in part, is coupled out, and visible radiation is deflected through a second light-conducting passageway which extends at an angle to the first light-conducting passageway for focusing the visible radiation on an illumination probe via an optical system comprised of a dimming disk for selective control of light intensity of the visible radiation, and a second optical lens.

Suitably, the second light-conducting passageway so guides the visible radiation that the visible radiation penetrates through the dimming disk and is subsequently directed through the second optical lens, or vice versa. The dimming disk may have several dim areas for control of the light intensity and is adjustable with respect to the second optical lens.

According to another feature of the present invention, the light intensity of the visible radiation deflected by the structure into the second light-conducting passageway can be controlled by the dim areas of the dimming disk, a color filter, or a fluorescence filter.

Suitably, the first optical lens may have a convexly arched surface at a side facing the light source, and the second optical lens may have a convexly arched surface at a side facing the structure and the dimming disk.

According to another aspect of the present invention, an apparatus for carrying out the novel and inventive process includes a light source; and at least one light-conducting system which guides light radiating from the light source along a first light-conducting passageway oriented in a direction of the path of light, and along a second light-conducting passageway extending at an angle to the first light-conducting passageway, whereby the first light-conducting system includes a first optical lens positioned at an entry side into the first light-conducting passageway, a reflector positioned at an exit side of the first light-conducting passageway for deflecting visible light into the second light-conducting passageway, and an optical assembly, disposed in the second light-conducting passageway, and comprised of a dimming disk, adjustable with respect to the second light-conducting passageway, for selective control of light intensity of the visible radiation, and a second optical lens for focusing the deflected radiation.

The provision of an apparatus according to the present invention, allows the use of a single central light source for radiating light, for example through two separate light-conducting systems that can be used for connection of a first ophthalmoscopic illumination probe for a basic illumination as well as connection of a second ophthalmoscopic illumination probe for illumination of a surgical site. Preferably, the second light-conducting passageway of each system has incorporated therein a dimming disk so that both light rays, focused at the exit of the light-conducting passageways, can be independently controlled from one another by the dimming disks. Suitably, a color filter, e.g. a green filter, may be arranged at the dimming disk in one light-conducting passageway, while a fluorescent filter may be arranged at the dimming disk of the other light-conducting passageway, whereby the operation of both filters can be executed simultaneously or separate from one another.

The dimming disk may be made of heat-resistant glass and printed or metallically coated with heat-resistant or ceramic color so as to ensure a substantially uniform decreasing or increasing illumination at constant diameter of the cone of light, in dependence on the direction of rotation and position of the dimming disk. The dimming disk is capable of allowing a maximum light transparency of 100% and subsequent even dimming action up to a point when effectively no light can penetrate.

According to another feature of the present invention, the light source is an arc lamp which compared to a halogen lamp has a significantly longer life and generates significantly less heat. Also, the arc lamp has an advantageous light spectrum which radiates fairly evenly over the entire visible range and has a maximum at 500 nm in the green spectrum in which the human eye has the greatest sensitivity to color.

BRIEF DESCRIPTION OF THE DRAWING

The above and other objects, features and advantages of the present invention will now be described in more detail with reference to the accompanying drawing, in which.

DETAILED DESCRIPTION OF PREFERRED EMBODIMENTS

Throughout all the Figures, same or corresponding elements are generally indicated by same reference numerals.

Figure 1:
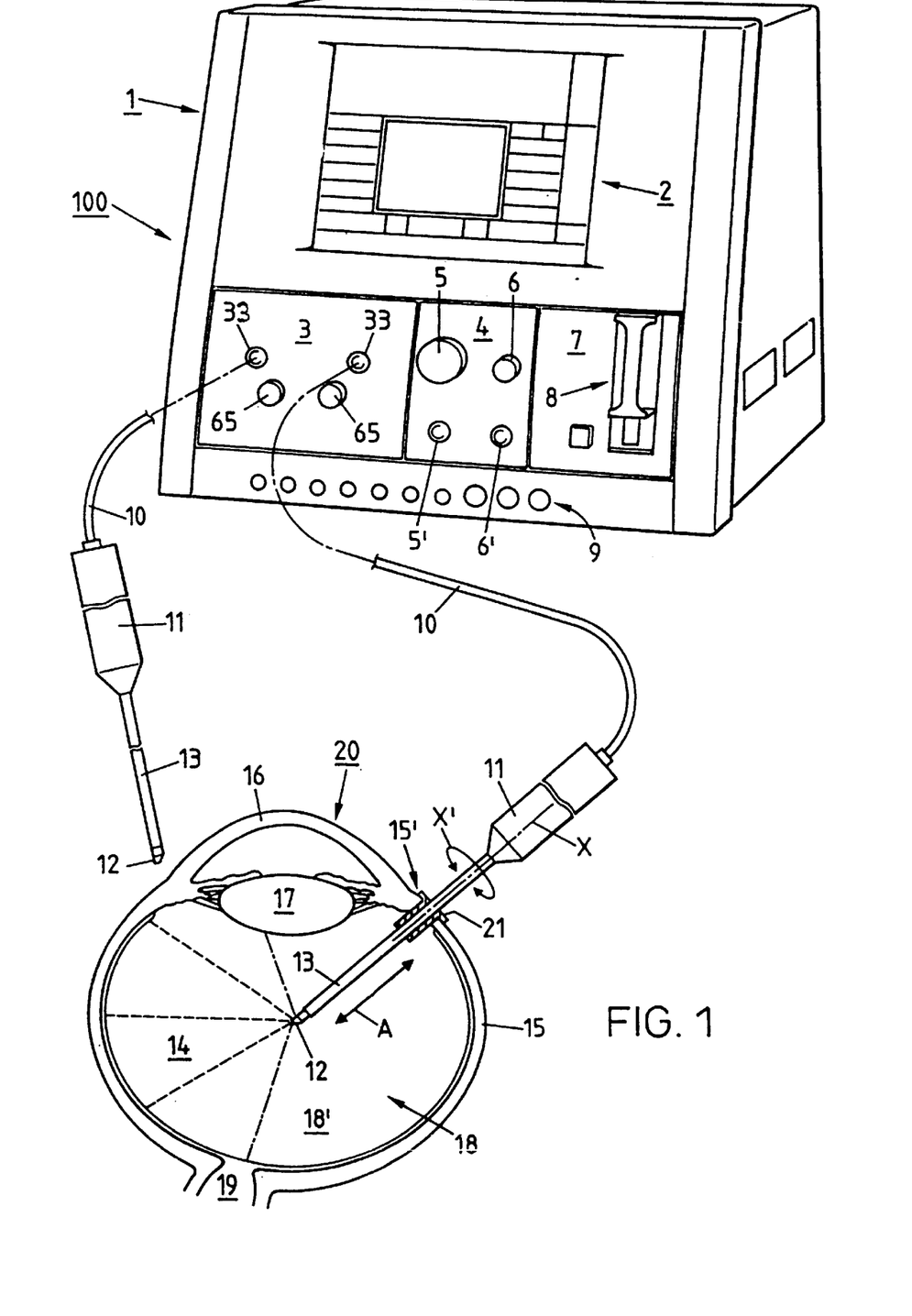
FIG. 1 is a perspective illustration of an ophthalmologic device having incorporated therein an illumination unit according to the present invention for operating at least one ophthalmoscopic illumination probe.
Figure 2:
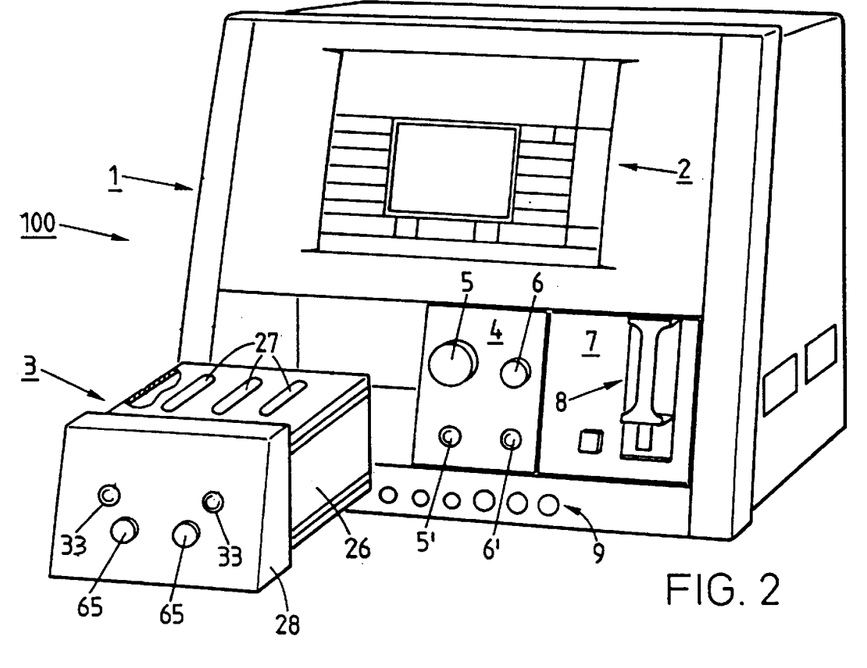
FIG. 2 is a perspective illustration of the ophthalmologic device of FIG. 1, with the illumination unit being partially withdrawn.

Turning now to the drawing, and in particular to FIG. 1, there is shown a schematic perspective illustration of an exemplified ophthalmologic device, generally designated by reference numeral 100, in particular for use in microsurgical procedures on the eye of a living being. The ophthalmologic device 100 includes a housing 1 which has a front console comprised of several side-by-side compartments for receiving functional units or modules 3, 4, 7, 8 to perform particular surgical procedures. The modules 3, 4, 7, 8 are designed as cassettes that can be inserted and withdrawn from the compartments for exchange, when necessary, as indicated in FIG. 2. Incorporated in the housing 1 above the modules 3, 4, 7, 8 is a display unit 2 which may have various control elements in the form of keys, push buttons or the like (not shown in detail). A series of neighboring jacks 9 is secured to the housing 1 beneath the modules 3, 4, 7, 8 for attachment of additional instruments. FIG. 2 shows by way of example the ability to withdraw or insert the modules The module 3 represents an illumination unit which includes on its front side two adjustment knobs 65 and two jacks 33 for connection of two ophthalmoscopic illumination probes 10 which may be provided in the form of optical conductors made of glass fibers or plastic fibers, and are used for illuminating the surgical site on an eye, generally designated by reference numeral 20. The eye 20 is shown schematically in FIG. 1 and includes the sclera 15, the cornea 16, the lens 17, the vitreous body 18 with the cavity 18', and the optical nerve bundle 19. One of the illumination probes 10 is inserted with its housing-distal end into the cavity 18' while the other illumination probe 10 is arranged at a distance to the eye 20 so that one of the illumination probes 10 can be used for basic illumination while the other one of the illumination probes 10 can be used to lighten the surgical site.

Each illumination probe 10 has attached thereon a casing 11 which forms a handle and supports a hollow needle 13. The illumination probe 10 thus penetrates in axial direction the casing 11 and the hollow needle 13 and has an end 12 so formed that light exits in a largest possible cone of light 14. A cannula 21 is inserted in the zone of the pars plana 15' for guiding the hollow needle 13 into the cavity 18' of the vitreous body 18 and allowing a rotation about the longitudinal axis X in direction of double arrow X' as well as an axial displacement in direction of double arrow A with respect to the sclera 15 of the eye 20. Both illumination probes 10 together with much other additional attached elements do not form part of the present invention and thus have not been described in more detail for sake of simplicity.

The module 4 represents a pressure unit which has a jack 5' for attachment of a conduit (not shown) that is connected to a pressure gas source, and an adjustment knob 5 for regulating the intraocular pressure (IOP) of the eye during the surgical procedure. A further jack 6' with adjustment knob 6 is provided for activating, for example, a visco-injection device (not shown).

The compartment next to the pressure unit 4 receives a plug-in cassette 8 which contains the irrigation and aspiration unit 7. The cassette 8 includes several tubes (not shown) and is engageable with an internal peristaltic pump when being inserted in the compartment of the housing 1. A specific construction and manner of operation such an irrigation and aspiration unit 7 is fully described, for example, in U.S. Pat. No. 5,454,783.

Figure 3:
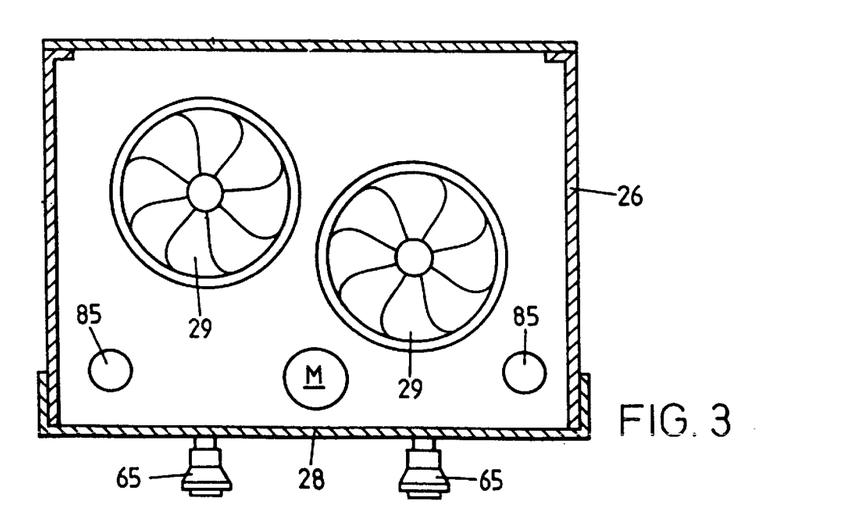
FIG. 3 is a partially sectional view of the illumination unit, showing in more detail some functional parts thereof.

As shown in FIG. 2, the illumination unit 3 includes a casing 26 which is closed off at the front by a cover 28 that carries the adjustment knobs 65 and has the jacks 33. The top of the casing 26 is formed with venting slots 27 that communicate with the interior space of the casing 26. Received in the bottom portion of the casing 26 are, for example, two fans 29 (FIG. 3) which are driven electromotorically for cooling the interior space of the casing 26 and the functional parts, such as light source 40 (FIG. 4), contained therein and described in more detail hereinafter. Cooling air, produced by the fans 29, is thus blown into the interior space and exits through the upper slots 27. Reference numeral 85 refers to sensors for monitoring the temperature in the interior space of the casing 26. The sensors 85 are coupled to the fans 29 and so operated that one of the sensors 85 is used for increasing the output of the fans 29 when the temperature inside the casing 26 exceeds approximately 50° C. while the other one of the sensors 85 can be used to shut down the illumination unit 3, i.e. the light source 40, when the temperature inside the casing 26 reaches approximately 70° C. Optionally, the operating time of the light source 40 may also be monitored, so that an acoustic or visual signal will be triggered when the operating time is exceeded. Suitably, a visual warning signal is indicated on the display unit 2.

Figure 4:
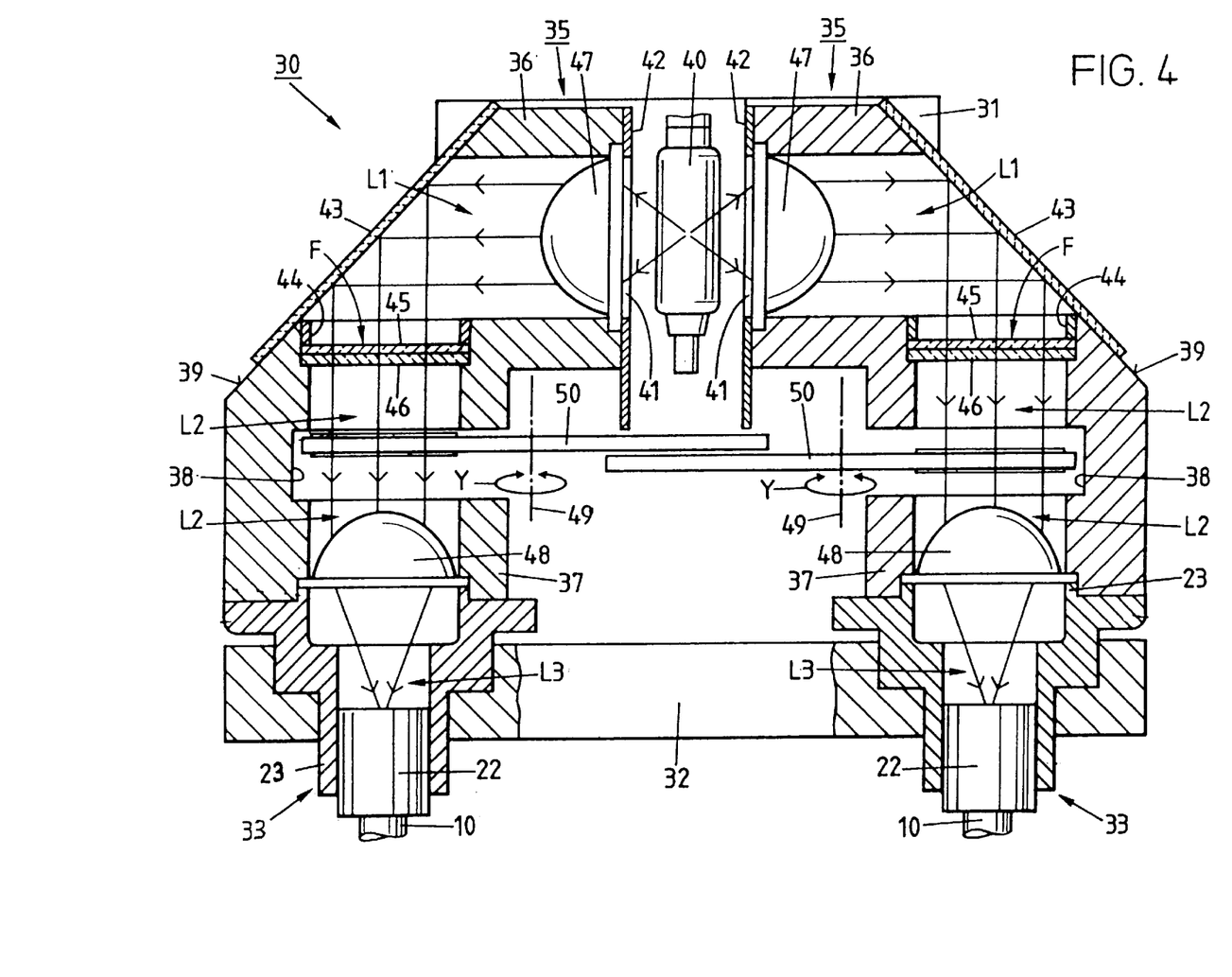
FIG. 4 is a sectional view of the illumination unit, illustrating the light-conducting system for the illumination probe.

Turning now to FIG. 4, there is shown a sectional view of a light-conducting system 30, accommodated in the casing 26 of the module 3, for the illumination probes 10. The light-conducting system 30 includes the light source 40 which is replaceably secured and radiates light to two spaced-apart assemblies 35 secured as mirror images of one another to one another on a base plate 31 via suitable screws (not shown) or the like so as to be exchangeable. For sake of simplicity, the light source 40 is shown only schematically, without illustration of the socket. Both assemblies 35 are of identical construction, so that only one assembly 35 will be described hereinafter in detail, and it will be understood by persons skilled in the art that a description of one assembly is equally applicable to the other assembly.

The assembly 35 has an angular, generally inverted L-shaped configuration to realize a deflection of light radiating from the light source 40, and includes a horizontal leg 36, which defines a light-conducting passageway L1, and a vertical leg 37, which extends at a right angle to the leg 36. The vertical leg 37 defines a light-conducting passageway L2 which thus extends at an angle, preferably at a right angle, to the light-conducting passageway L1. Formed in the leg 37 is a substantially gap-shaped recess 38 for dividing the light-conducting passageway L2 in two partial sections. The recess 38, which extends substantially transversely to the passageway L2, supports a dimming disk 50 which is connected to a drive 80 for rotation about an axis 49, as indicated by double arrow Y.

Operation of the dimming disk 50 is realized by turning the adjustment knob 65 on the front cover 28 to activate the drive 80, for example an electromotor M coupled to a cylindrical gear mechanism, as will be described in more detail with reference to FIG. 5.

The leg 37 of the assembly 35 terminates upon a flanged annular insert 23 of the jack 33 which insert 23 is detachably secured at one end to the assembly 35 and detachably fitted, for example by screws, in a bore 34 (FIG. 5) of the support plate 32, thereby ensuring a coaxial alignment of the jack 33 with the light-conducting passageway L2. The insert 23 of the jack 33 defines in axial direction a light-conducting passageway L3 which extends the light-conducting passageway L2. A contact socket 22 of the illumination probe 10 is insertable in the insert 23 of the jack 33.

The light source 40 is suitably formed by an electric arc lamp (micro low-pressure "longlife" bulb) with an output of 20 to 100 watts, preferably with an output of 50 watts. Compared to light sources utilized in conventional illumination units, the light source 40 in the form of an arc lamp produces a relatively high light flux which is approximately threefold of a comparable halogen lamp of 50 watts. Further, the described light source 40 displays a relatively low power consumption and thus generates less heat than other light sources.

Tests have shown that the use of an arc lamp 40 results in a service life which exceeds by about 30 times the service life of a halogen lamp, used heretofore. Compared to a halogen lamp which radiates in the infrared range and thus generates much heat, the light spectrum of the arc lamp 40 radiates fairly evenly over the entire visible range and has a maximum at 500 nm in the green spectrum in which the human eye has the greatest sensitivity to color. Moreover, the arc lamp 40 converts the energy of 50 watts in substantially more visible light while a halogen lamp generates and radiates more heat.

Arranged, preferably as near as possible to the light source 40 is an optical lens 47 which forms the entry into the light-conducting passageway L1 of the leg 36. At its light source distal side, the lens 47 is formed with a convex outwardly arched or spherical or parabolical surface. At the opposite light source proximal side, the lens 47 is detachably mounted to a disk 42 which is provided with a sufficiently sized aperture 41 to allow passage of light radiating from the light source 40. Light is directed by the lens 47 to travel through light-conducting passageway L1 onto a structure in the form of a mirror 43 which is so configured as to allow passage of heat while deflecting visible light. The mirror 43 may be made of heat-resistant material, preferably heat-resistant glass. A filter effect is realized through vacuum-coating (reflection R 97% at 425 to 600 nm; transparency T 50% at 685 nm; transparency T 80% at 750 to 2500 nm, nm=nanometer as unit of the wavelength).

The mirror 43 in the light-conducting passageway L1 is detachably mounted, e.g. by screws, to a slanted outer surface 39 of the assembly 35 and thus extends at an angle of 45° with respect to the light-conducting passageway L1. Optionally, the mirror 43 may be combined with a filter unit (not shown), for example, a filter unit comprised of a heat filter and a UV filter. In this manner, the heat filter can convey heat radiation to the outside, while the UV filter can absorb remaining UV radiation.

As further shown in FIG. 4, a filter unit F is placed in the light-conducting passageway L2 and secured in the leg 37 in immediate proximity to the light-conducting passageway L1. In the non-limiting example involved here, the filter unit F includes a heat filter 45 and a subjacent UV-filter 46 and is detachably secured by a retention ring 44 in the light-conducting passageway L2. The heat filter 45 may be made, for example, from heat-resistant glass and blocks incident heat coming from the mirror 43. Suitably, the heat filter is vacuum coated as follows: transparency T<1% up to 380 nm; T=50% at 400 nm, T>80% at 425–680 nm, T=50% at 730 nm, T<3% at 800–1150 nm, T<10% at 1150–2500 nm. The associated UV filter 46 absorbs UV radiation up to 440 nm (50%) that is hazardous to the human eye.

The dimming disk 50 received in the recess 38 of the leg 37 is followed in the light-conducting passageway L2 by an optical lens 48 which is positioned at the end of the light-conducting passageway L2 and secured to the leg 37. The optical lens 48 has on its dimming disk facing side a spherical surface and is held on its dimming disk distal side in the flanged insert 23 of the jack 33. The dimming disk 50 is preferably made from heat-resistant glass and suitably imprinted with heat-resistant or ceramic color or metallically coated to realize various dim areas, as will be described in more detail with reference to FIG. 10.

The light-conducting system of the illumination unit 3 operates as follows: Light radiating from the light source 40 travels through the optical lens 47 and is directed into parallel alignment through the light-conducting passageway L1 onto the mirror 43. Radiation of about 750 nm to 2500 nm (heat) passes through the mirror 43 and is coupled out, while visible radiation of about 425 nm to 685 nm is deflected by the mirror 43 into the light-conducting passageway L2. The visible radiation first passes in the light-conducting passageway L2 the heat filter 45 which reflects remaining heat radiation of e.g. 730 nm as well as UV radiation below 400 nm onto the mirror 43 from where it is ultimately conveyed to the outside or absorbed. Radiation of below about 440 nm, that may still be present, is absorbed by the subsequent UV filter. Remaining light rays are directed by the dimming disk 50, swung into the light-conducting passageway L2 by the drive 80 to position a suitable dim area in the travel path of the radiation for selective control of the light intensity, onto the optical lens 48 which focuses the light for the illumination probe 10. As indicated in FIG. 5, the dimming disk 50 may be coupled with a filter 60, for example a color filter or fluorescence filter. Suitably, the dimming disk 50 of one assembly 35 may be coupled with a color filter, while the dimming disk 50 of the other assembly 35 may be coupled with a fluorescence filter.

Persons skilled in the art will understand that it is certainly within the scope of the present invention to install the dimming disk 50 and the optical lens 48 in reverse order, i.e. visible radiation travels in the light-conducting passageway L2 in a first phase through the lens 48 and subsequently through the dimming disk 50 for selective control of the light intensity, before reaching the illumination probe 10.

The lenses 47, 48 may be formed as planoconvex lenses, with the side of the lenses facing the light-conducting passageways L1 and L2, respectively, having a convexly arched or spherical or parabolic configuration. It is further within the scope of the present invention to so modify the lens 47 as to be slightly convex on the side facing the light source 40. Moreover, it may be suitable to configure the lenses 47, 48 either of biconvex configuration or concavo-concave configuration.

Figure 5:
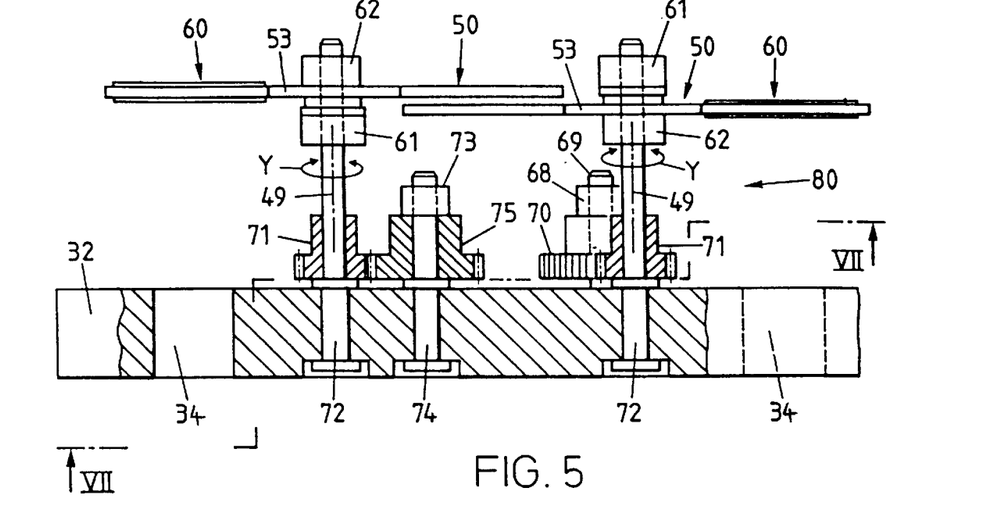
FIG. 5 is a sectional cutaway view of the illumination unit, showing in detail the area of rotatable dimming disks of two light-conducting systems, and their drive.

Referring now to FIG. 5, it can be seen that the drive 80 for rotating the dimming disks 50 with associated filters 60 of both assemblies 35 includes two shafts 72 positioned in spaced-apart parallel relationship and having one end secured in the retention plate 32. The other end of the shafts 72 carries the dimming disks 50, respectively. A nut 61 and a set collar 62 secure each dimming disk 50 to the shaft 72 against a displacement in axial direction and realize a fixed rotative engagement between the dimming disk 50 and the shaft 72.

Figure 6:
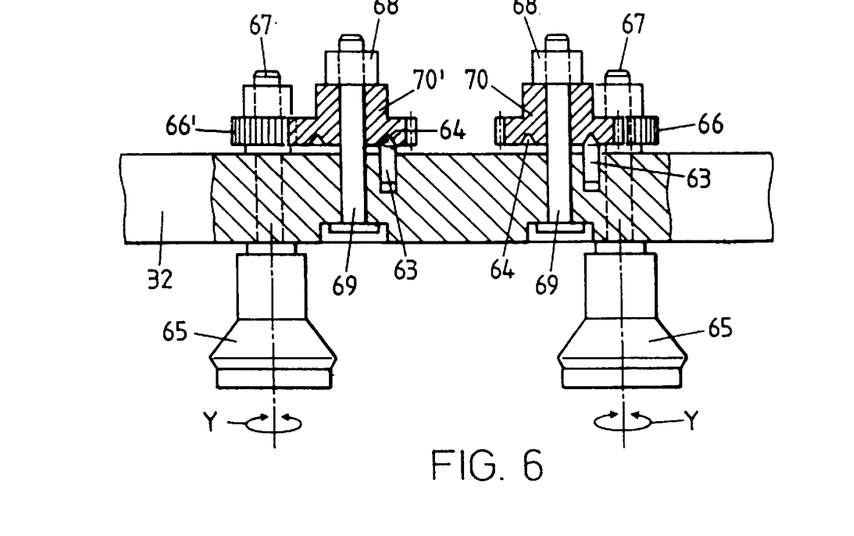
FIG. 6 is another sectional view of the area of the dimming disks and their drive.
Figure 7:
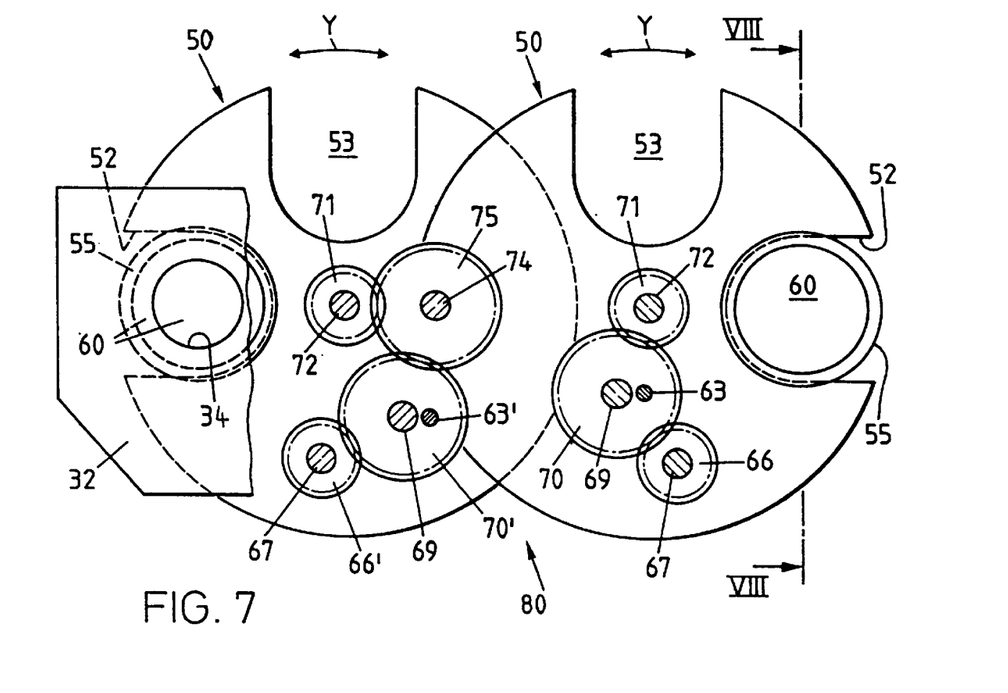
FIG. 7 is a sectional view of the drive, taken along the line VII—VII in FIG. 5.

Placed in fixed rotative engagement on each shaft 72 at an axial distance to the respective dimming disk 50 is a gear 71. The gear 71 on one of the shafts 72 (e.g. the shaft on right hand side in FIG. 5) is in mesh with external teeth of a drive gear 66 via an index wheel 70, while the gear 71 of the other one of the shafts 72 is in mesh with external teeth of a drive gear 66' via a cylindrical gear 75 and an associated index wheel 70', as best shown in FIG. 7. As shown in FIG. 6, the drive gears 66, 66' are mounted in fixed rotative engagement on respective ends of shafts 67 which carry at their other ends the adjustment knobs 65. Thus, the adjustment knobs 65 turn analogous to the dimming disks 50. The cylindrical gear 75 is mounted on a shaft 74, supported in the retention plate 32, and secured against axial displacement by a set collar 73.

The index wheels 70, 70' are each mounted on a shaft 69 and formed on their side facing the retention plate 32 with several circumferentially spaced notches 64 for engagement of an index pin 63 which is mounted in the retention plate 32. A set collar 68 secures the index wheel 70; 70' against axial displacement on the shaft 69. When turning the index wheel 70; 70', the index pin 63 is pushed out of the respective notch 64 in opposition to the force of a spring element (not shown) for engagement into a neighboring notch 64. In this manner, actuation of the adjustment knobs 65 activates the drive 80 to rotate the dimming disks 50 and to thereby select the desired dim area. Activation of the drive 80 may also be realized through operation of the electro-motor M (FIG. 3), separately from or together with the actuation of the adjustment knobs 65.

Turning now to FIG. 7, it can be seen that the dimming disk 50 of each assembly 35 is formed with two recesses 52, 53 which are offset to one another by 90°. In the exemplified configuration, involved here, the recess 52 of the dimming disk 50 of one assembly 35 accommodates a filter 60 in the form of a color filter, while the recess 52 of the dimming disk 50 of the other assembly accommodates a filter 60 in the form of a fluorescence filter. The filters 60 are secured to the dimming disks 50 by suitable retaining rings 55.

Figure 8:
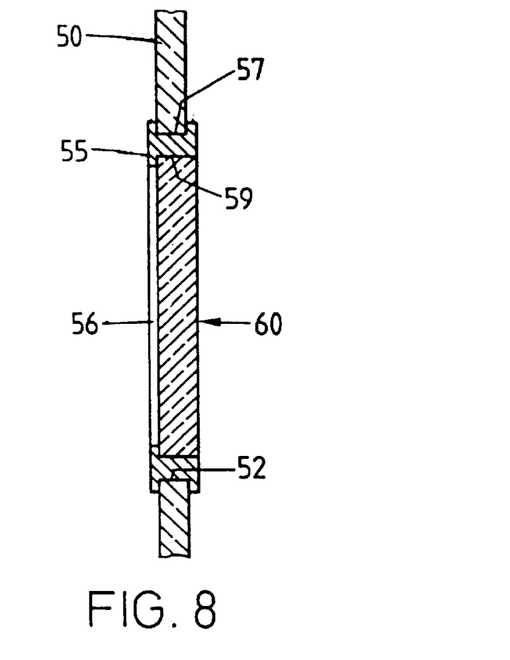
FIG. 8 is a sectional view, on an enlarged scale, of a dimming disk, taken along the line VIII—VIII in FIG. 7 and equipped with a filter.

Referring now to FIG. 8, there is shown an enlarged sectional view of the dimming disk 50, and it can be seen that the retaining ring 55 is formed with a circular opening 56 and circular recess 59 for receiving the filter 60 (color filter) which is exchangeably mounted in the recess 59 of the retaining ring 55. Formed on the outer perimeter of the retaining ring 55 is a circumferential U-shaped groove 57 which engages the boundary wall of the recess 52 to hold the retaining ring 55 for the filter 60 in the recess 52 of the dimming disk 50.

Figure 9:
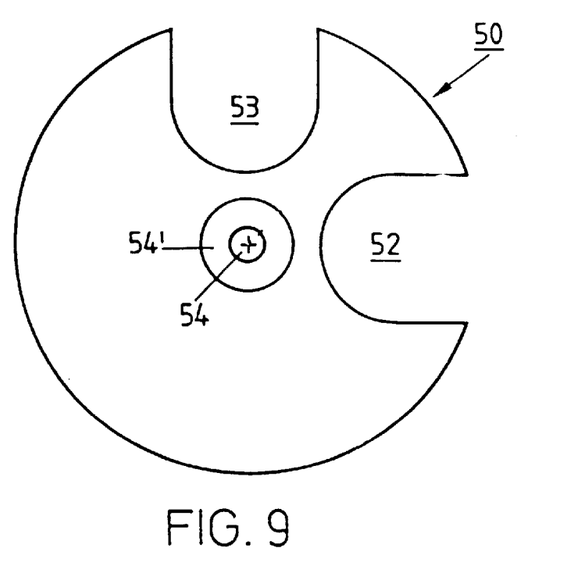
FIG. 9 is a schematic top plan view of a blank dimming disk.
Figure 10:
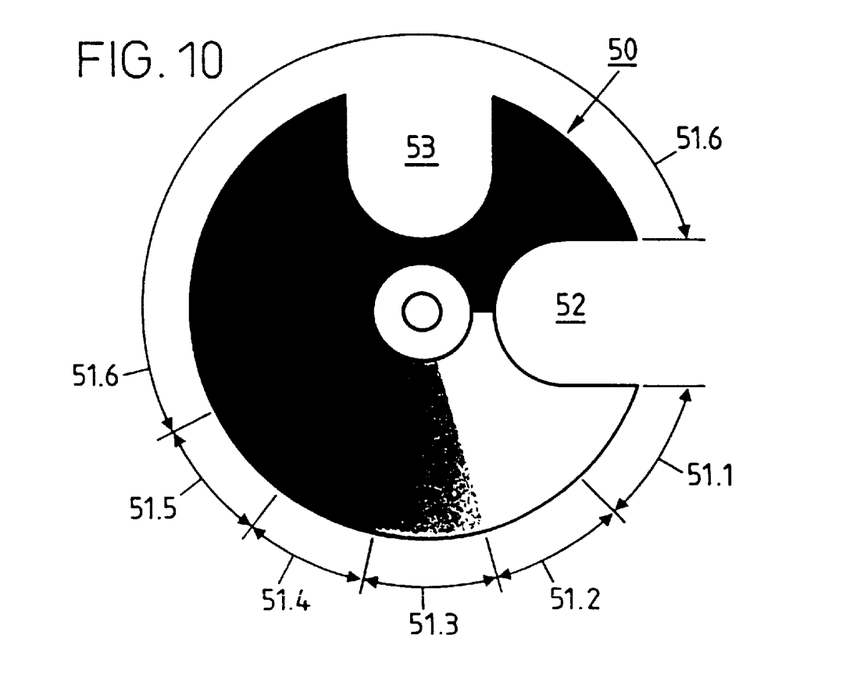
FIG. 10 is a schematic top plan view of the dimming disk of FIG. 9, provided with a number of dim areas for use in the illumination unit of FIG. 1.

FIG. 9 shows a top plan view of the dimming disk 50 as a blank. The blank has a central bore 54, which is demarcated by a circular ring shaped boundary surface 54', and is formed with the recesses 52, 53 in 90° offset relationship, whereby recess 52 is adapted for receiving the retaining ring 55 for accommodation of the filter 60. The blank for the dimming disk 50 can then be provided with several dim areas for controlling the light quantity traveling through the dimming disk 50 in dependence on its direction of rotation. As shown in FIG. 10, the individual dim areas on the dimming disk 50 blend, preferably continuously, into one another and are applied in the blank by conventional screen printing. The individual dim areas, denoted 51.1 to 51.6 have sector-shaped configuration and have a dot density that increases, preferably continuously, from dim area to dim area in clockwise direction. The dot density of the dim area 51.6 is so selected that the area, interrupted by the recess 53, is substantially light-impervious (black). Including the recesses 52, 53, the dimming disk 50 thus exhibits eight zones, with recess 53 ensuring a maximum transparency of 100%, while recess 52 is used for receiving the filter 60.

The dimming disk 50 of each assembly 35 are made preferably of heat-resistant glass and, for example, imprinted with heat-resistant or ceramic color, or metallically coated. Preferably, the recess 52 of one of the dimming disks 50 has accommodated therein a color filter (green filter) which permits diagnosis of relatively thin membranes in the human eye, while the recess 52 of the other one of the dimming disks 50 has accommodated therein a fluorescence filter which allows a particular method of visual recognition of blood vessels in the eye when injecting a contrast agent which so interacts with light from the fluorescence filter that the light illuminates in a different wavelength range and thus can be recognized by an viewing filter arranged on a microscope. The viewing filter bars light from the fluorescence filter and permits passage of the light of the contrast agent.

While the invention has been illustrated and described as embodied in a method of and apparatus for focusing a light flux, it is not intended to be limited to the details shown since various modifications and structural changes may be made without departing in any way from the spirit of the present invention.

What is claimed as new and desired to be protected by Letters Patent is set forth in the appended claims:

1. A method of focusing a light flux radiating from a light source; comprising the steps of:

directing a light flux by a first optical lens through a first light-conducting passageway onto a structure by which heat is, at least in part, coupled out; and deflecting visible radiation by the structure through a second light-conducting passageway which extends at an angle to the first light-conducting passageway for focusing the visible radiation on an illumination probe via an optical system comprised of a dimming disk for selective control of light intensity of the visible radiation, and a second optical lens.

2. The method of claim 1, wherein the second light-conducting passageway so guides the visible radiation that the visible radiation penetrates through the dimming disk and is subsequently directed through the second optical lens.

3. The method of claim 1, wherein the second light-conducting passageway so guides the visible radiation that the visible radiation is directed through the second optical lens and subsequently penetrates through the dimming disk.

4. The method of claim 1 wherein the dimming disk has several dim areas for control of the light intensity and is adjustable with respect to the second optical lens.

5. The method of claim 4 wherein the light intensity deflected by the structure into the second light-conducting passageway is controllable by an element selected from the group consisting of said dim areas of the dimming disk, a color filter, and a fluorescence filter.

6. The method of claim 1 wherein the light intensity deflected by the structure into the second light-conducting passageway passes through a filter unit comprised of a heat filter and a UV filter and subsequently through an element selected from the group consisting of dim areas of a dimming disk, a color filter, and a fluorescence filter, for control of the light intensity.

7. The method of claim 1 wherein the first optical lens has a convexly arched surface at a side facing the light source, and the second optical lens has a convexly arched surface at a side facing the structure and the dimming disk.

8. Apparatus for focusing a light flux, comprising:
   a light source; and
   a first light-conducting system guiding light radiating from the light source along a first light-conducting passageway oriented in a direction of the path of light, and along a second light-conducting passageway extending at an angle to the first light-conducting passageway, said first light conducting system including a first optical lens positioned at an entry side into the first light-conducting passageway, a deflector positioned at an exit side of the first light-conducting passageway for deflecting visible light into the second light-conducting passageway, and an optical assembly, disposed in the second light-conducting passageway, and comprised of a dimming disk, adjustable with respect to the second light-conducting passageway, for selective control of light intensity of the visible radiation, and a second optical lens for focusing the deflected radiation.

9. The apparatus of claim 8 wherein the dimming disk is positioned in the second light-conducting passageway upstream of the second optical lens, as viewed in the direction of the light radiation deflected by the structure.

10. The apparatus of claim 8 wherein the second optical lens is positioned in the second light-conducting passageway upstream of the dimming disk, as viewed in the direction of the light radiation deflected by the structure.

11. The apparatus of claim 8 wherein the first optical lens has a concavely arched surface at a light source distal side, and the second optical lens has a concavely arched surface at a structure proximal side.

12. The apparatus of claim 8 wherein the first and second optical lenses have each a plano-arched convex configuration, with the first optical lens having a convexly arched surface at a light source distal side, and with the second optical lens having a convexly arched surface at the structure proximal side.

13. The apparatus of claim 8 wherein the first and second optical lenses have each a plano-arched configuration, with the first optical lens being formed at a light source distal side with one of a spherical and non-spherical configuration, and with the second optical lens being formed at the structure proximal side with one of a spherical and non-spherical configuration.

14. The apparatus of claim 8 wherein the first light-conducting system is disposed on one side of the light source at a distance thereto and has an angular configuration, with a first section forming the first light-conducting passageway at a distance to the light source, and a second section forming the second light-conducting passageway, and further comprising a second light-conducting system disposed on the other side of the light source at a distance thereto and having an angular configuration, said second light-conducting system having a same configuration as the first light-conducting system, with the second sections of the first and second light-conducting systems extending at a distance to one another.

15. The apparatus of claim 14 wherein the second sections of the first and second light-conducting systems extend parallel to one another.

16. The apparatus of claim 8, and further comprising a filter unit, disposed in the second light-conducting passageway in an area of the deflector, and including a heat filter and a UV filter.

17. The apparatus of claim 8 wherein the deflector is a mirror which is capable of coupling out heat and deflecting visible light.

18. The apparatus of claim 8 wherein the dimming disk has several dim areas and is formed with two recesses arranged offset to one another in circumferential direction, with one of the recesses destined for exchangeably receiving a filter which is swingable into the second light-conducting passageway.

19. The apparatus of claim 14 wherein the dimming disk of the first light-conducting system and the dimming disk of the second light-conducting system have each several dim areas and are formed with two recesses arranged offset to one another in circumferential direction, wherein at least one of the recesses of one of the first and second light-conducting systems is destined for receiving a color filter and at least one of the recesses of one of the first and second light-conducting systems is destined for receiving a fluorosecence filter.

20. The apparatus of claim 19 wherein the color filter and the fluorosecence filter are exchangeably received in the recesses of the dimming disks of the first and second light-conducting systems.

21. The apparatus of claim 18 wherein the dim areas have a substantially sector-like configuration and exhibit a continuously increasing spot density from a first dim area to a last dim area as viewed in circumferential direction, with the last dim area being black for realizing a substantial imperviousness to light.

22. The apparatus of claim 18 wherein the dimming disk is supported by an axle for rotation about a longitudinal axis thereof so that the dim areas and the filter are selectively positionable in the second light-conducting passageway for controlling the light intensity.

23. The apparatus of claim 22, and further comprising a drive, activated by adjustment knobs, for rotating the dimming disk about the longitudinal axis.

24. The apparatus of claim 23 wherein the drive includes an electric motor.

25. The apparatus of claim 23 wherein the drive is a gear mechanism.

26. The apparatus of claim 25 wherein the gear mechanism is a cylindrical gear mechanism.

27. The apparatus of claim 8 wherein the first light-conducting system and the light source form a self-contained assembly for attachment of an illumination probe.

28. The apparatus of claim 8 wherein the light source is an arc lamp.

* * * * *